United States Patent
Xu et al.

(10) Patent No.: US 11,773,373 B2
(45) Date of Patent: Oct. 3, 2023

(54) METHOD FOR AMPLIFYING CD8+T CELLS AND CELL SUBPOPULATIONS THEREOF IN-VITRO

(71) Applicant: Shanghai Innovative Chang'An Biological Technology Co., Ltd., Shanghai (CN)

(72) Inventors: Jianqing Xu, Shanghai (CN); Xiaoyan Zhang, Shanghai (CN); Chenli Qiu, Shanghai (CN)

(73) Assignee: Shanghai Innovative Chang'An Biological Technology Co., Ltd., Shanghai (CN)

( * ) Notice: Subject to any disclaimer, the term of this patent is extended or adjusted under 35 U.S.C. 154(b) by 614 days.

(21) Appl. No.: 16/478,580

(22) PCT Filed: Dec. 15, 2017

(86) PCT No.: PCT/CN2017/116342
§ 371 (c)(1),
(2) Date: Jul. 17, 2019

(87) PCT Pub. No.: WO2018/133598
PCT Pub. Date: Jul. 26, 2018

(65) Prior Publication Data
US 2020/0063103 A1    Feb. 27, 2020

(30) Foreign Application Priority Data
Jan. 17, 2017 (CN) .......................... 201710034922.8

(51) Int. Cl.
*C12N 5/0783* (2010.01)
*C12N 5/00* (2006.01)

(52) U.S. Cl.
CPC .... *C12N 5/0638* (2013.01); *C12N 2501/2302* (2013.01); *C12N 2501/2307* (2013.01); *C12N 2501/2315* (2013.01); *C12N 2501/998* (2013.01); *C12N 2501/999* (2013.01); *C12N 2509/10* (2013.01)

(58) Field of Classification Search
None
See application file for complete search history.

(56) References Cited

U.S. PATENT DOCUMENTS

| | | | |
|---|---|---|---|
| 2006/0205069 A1* | 9/2006 | June | C07K 16/2812 436/524 |
| 2016/0008460 A1 | 1/2016 | Knolle et al. | |
| 2017/0114321 A1* | 4/2017 | Berenson | C12N 5/0087 |
| 2017/0233454 A1* | 8/2017 | Li | A61K 39/0011 424/134.1 |
| 2018/0148690 A1* | 5/2018 | Gros | A61K 38/1703 |
| 2018/0169224 A1* | 6/2018 | McNeel | A61K 39/0011 |
| 2019/0270817 A1* | 9/2019 | Ali | C12N 15/85 |
| 2020/0087625 A1* | 3/2020 | Carson | A61P 35/04 |
| 2020/0248140 A1* | 8/2020 | Cohen | A61K 39/001156 |
| 2021/0171909 A1* | 6/2021 | Golovina | C07K 16/2803 |

FOREIGN PATENT DOCUMENTS

| | | |
|---|---|---|
| CN | 105451766 A | 3/2016 |
| WO | WO-2009/062001 A1 | 5/2009 |

OTHER PUBLICATIONS

Chinese Patent Application No. 201710034922.8, Office Action, dated Apr. 11, 2019.
International Application No. PCT/CN2017/116342, International Search Report, dated Mar. 19, 2018.
Wang et al., CD3/CD28 In vitro expansion of peripheral blood T lymphocytes by immuno magnetic beads, Chin. J. Cell. Mol. Immunol., 30(10):1090-2 (2014).
Partial Translation of Chinese Patent Application No. 201710034922. 8, Office Action, dated Apr. 11, 2019.

\* cited by examiner

*Primary Examiner* — Michail A Belyavskyi
(74) *Attorney, Agent, or Firm* — MARSHALL, GERSTEIN & BORUN LLP (57) ABSTRACT

Disclosed is a method for rapidly amplifying CD8+T cells and functional cell subpopulations thereof in vitro. A TLR1/2 agonist, a TLR2/6 agonist and a TLR5 agonist or a combination of above agonists is added to a conventional culture system for in-vitro amplification of CD8+T cells. Recombinant cytokines IL-2, IL-7 and IL-15 as well as magnetic beads coated with an anti-human CD3 antibody and an anti-human CD28 antibody can be further added to the culture system for continuous co-stimulation.

7 Claims, 6 Drawing Sheets

Specification includes a Sequence Listing.

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Pam2

<400> SEQUENCE: 1

Cys Gly Asp Pro Lys His Pro Lys Ser Phe
1               5                   10
```

METHOD FOR AMPLIFYING CD8+T CELLS AND CELL SUBPOPULATIONS THEREOF IN-VITRO

INCORPORATION BY REFERENCE OF MATERIAL SUBMITTED ELECTRONICALLY

This application contains, as a separate part of disclosure, a sequence listing in computer-readable form (filename: 54506_SeqListing.txt; 632 bytes; created: Nov. 18, 2019) which is incorporated by reference in its entirety.

TECHNICAL FIELD

The present invention belongs to the field of cell biology, and particularly relates to a method for inducing in vitro amplification of CD8+ T cells and functional cell subpopulations thereof.

BACKGROUND

CD8+ T cells are important effector cells involved in anti-tumor and anti-infection immunity. Activated CD8+ T cells can rapidly release high concentrations of cytokines such as IFN-γ and IL-2, and have extensive immunomodulatory effects. In acute infection, CD8+ T cells are activated and substantially proliferate by antigenic stimulation and then differentiate into effector CD8+ T cells (CTL), which kill infected cells by secreting porforin and granzyme (Granzyme B) or induce apoptosis of infected cells by the Fas-FasL pathway. When pathogens are eliminated, a small part of effector CD8+ T cells differentiate into memory CD8+ T cells. When the same antigens appear again, the memory CD8+ T cells in the body will rapidly proliferate and differentiate into effector CTLs which can further eliminate the pathogens of infections.

CD8+ T cells are also one of the main effector cells of anti-tumor immunity in the body. It is one of the development directions of modern tumor immunotherapy to induce response of CD8+ T cells against tumor-specific antigens by active immunization with vaccine. However, the vaccine that can stimulate effective response of CD8+ T cells in the normal body is not ideal in the tumor-bearing body, which is associated with an immunosuppressive microenvironment formed by anergy or depletion of CD8+ T cells in local parts of tumors due to the fact that a plurality of immunoregulatory cells or factors are highly enriched or highly expressed in local parts of tumors. Tumor Infiltrating Lymphocytes (TIL) are tumor antigen-specific lymphocyte populations such as CD4+ T and CD8+ T found in tumor tissues, wherein CD8+ T cells have a tumor killing effect. The extent of TILs infiltrating around tumors and the proportion of CD8+ T cells are obviously positively correlated with good prognosis for the tumor patients.

During the process of chronic infection, as well as tumorigenesis and development, antigen-specific CD8+ T cells that cannot effectively differentiate into memory T cells due to persistent stimulation of antigens, gradually evolve into a group of cells with dysfunction which are known as depleted CD8+ T cells. On the surfaces of this group of cells, an inhibitory receptor PD-1, and other inhibitory receptors such as CD244 (2B4), LAG-3, CD160, TIM-3 and CTLA-4 are persistently and highly expressed. PD-1 has been recognized as a surface marker of a depleted T lymphocyte. Studies show that, in chronic infectious diseases, the combined blocking of PD-1 and CTLA-4, PD-1 and LAG-3 as well as PD-1 and Tim-3 can partially restore the biological function of CD8+ T cells; and for tumor antigen-specific CD8+ T cells, the combined blocking of PD-1 and Tim-3 or PD-1 and LAG-3 can also partially restore the function of the CD8+ T cells. Blocking these pathways can partially restore the function of depleted T cells, but fail to reverse the phenotype of depleted T cells into non-depleted T cells, leading to tumor recurrence and metastasis, which cannot achieve the purpose of radical cure.

Recent studies by Rosenberg S A have shown that PD1+ CD8+ T cells circulating in peripheral blood can specifically recognize melanoma antigens and have similar T cell antigen receptors (T cell receptors, TCR) to tumor-infiltrating specific CD8+ T cells that locally express PD-1 in tumors, thus PD-1 can be used as a biomarker for obtaining tumor-specific T cells from peripheral blood. This provides a new non-invasive strategy for treating cancer using tumor-specific lymphocytes or TCRs and provides a new approach to the development of personalized treatment.

In recent years, immunotherapy has developed very rapidly. Many cell therapies, such as those of CAR-T, DC-CIK, NKT and NK cells which are reinfused into patients after in-vitro amplification, have emerged continuously, and the corresponding cell culture and amplification methods also have been continuously improved. Currently, a main technique for amplifying patient cells is to stimulate cell proliferation using one or more cytokines such as interleukins IL-2, IL-7 and IL-15 in combination with an anti-CD3 antibody and an anti-CD28 antibody. For example, CD8+ T cells in AIDS patients or tumor patients are isolated, and an anti-CD3 antibody, IL-2 and IL-7 are used to stimulate the in-vitro amplification of memory CD8+ T cells. Compared with 200 IU/ml of IL-2, 5 ng/ml of IL-15 and 5 ng/ml of IL-7 can be added to a culture system for in-vitro amplification of TILs so as to obtain TILs with the same amplification numbers and in-vitro function. IL-15 and IL-7 are able to stimulate in-vitro proliferation of T lymphocytes, promote production of IFN-γ by CD8+ T cells, maintain the phenotype of central memory CD8+ T cells and reduce the number of regulatory T cells (CD4+CD25+Treg), therefore to play a beneficial role in controlling tumor cells. Accordingly, a low dose of IL-15 in combination with a low dose of IL-7 can be used instead of a high dose of IL-2 for in-vitro amplification of TILs. The addition of an anti-CD3 antibody to a culture system for amplification of melanoma TILs can significantly increase the amplification numbers of the TILs.

However, specific functional cell subpopulations such as PD-1+CD8+ T cells and TEM CD8+ T cells necessary for anti-tumor immunity are difficult to amplify under conventional culture conditions, and there has been no method for rapidly amplifying PD1+CD8+ T cells in vitro. It has been reported in the literature that the PD1+CD8+ T cells sorted from cancer patients have limited in-vitro amplification efficiency, and the amplified cells generally have a capacity of secreting IFN-γ of less than 20%. Thus, it is difficult to meet the needs of anti-tumor immunity and anti-infection immunity. How to further enhance the amplification efficiency of CD8+ T cells and PD1+CD8+ T cell subpopulations thereof, especially the ability to effectively amplify functional CD8+ T cells so as to enhance the anti-infection and anti-tumor effect is an urgent problem to be solved.

Accordingly, it will be a safe and effective method for disease treatment to rapidly and efficiently amplify CD8+ T cells and functional subpopulations thereof and reinfuse

SUMMARY OF THE INVENTION

A technical problem to be solved by the present invention is to develop a method for amplifying CD8+ T cells and functional cell subpopulations thereof, in particular, a method for amplifying PD-1+CD8+ T cells that are considered to be depleted. The addition of Toll-like receptor (TLR) agonists such as TLR1/2 agonists, TLR2/6 agonists and TLR5 agonists or a combination thereof can significantly enhance the in-vitro amplification efficiency of the CD8+ T cells, and allow the functional cell subpopulations such as PD-1+CD8+ T cells to be effectively amplified.

To solve the above technical problem, the present invention employs the following technical solution: providing a method for inducing amplification of CD8+ T cells and functional CD8+ T cell subpopulations thereof in vitro, wherein one or more TLR agonists are added to a culture system for CD8+ T cells and functional CD8+ T cell subpopulations, with the stimulation by an anti-human CD3 antibody or an anti-human CD28 antibody and various cytokines, the amplification efficiency and activation of the CD8+ T cells and the functional cell subpopulations thereof can be significantly enhanced.

The TLR agonists include, but are not limited to: TLR1/2 agonists, TLR2/6 agonists, TLR5 agonists as well as TLR3, TLR4, TLR7, TLR8 and TLR9 agonists, which can be used alone or in combination. The TLR1/2 agonists include, but are not limited to, Pam3CK4, the TLR2/6 agonists include, but are not limited to, FSL-1 and Pam2CGDPKHPKSF (SEQ ID NO: 1), and the TLR5 agonists include, but are not limited to, Flagellin. The anti-human CD3 antibody or the anti-human CD28 antibody is coated on magnetic beads for use. The anti-human CD3 antibody alone can be used in combination with the TLR agonists, or can be combined with the anti-human CD28 antibody and then used in combination with the TLR agonists. The cytokines include, but are not limited to, IL-2, IL-7 and IL-15, which can be used alone or in combination, and can be added simultaneously or sequentially to the culture system.

In addition, the functional CD8+ T cell subpopulations comprise sorted and purified PD-1+CD8+ T cells, sorted and purified CD137+CD8+ T cells, sorted and purified CD160+CD8+ T cells, sorted and purified naive CD8+ T cells, sorted and purified central memory CD8+ T cells, sorted and purified effector memory CD8+ T cells, sorted and purified effector CD8+ T cells, sorted and purified transitional memory CD8+ T cells, sorted and purified effector stem cell CXCR5+CD8+ T cells, and sorted and purified tissue-resident memory CD8+ T cells.

Preferably, when the PD-1+CD8+ T cells in the functional CD8+ T cell subpopulations are amplified in vitro, the anti-human CD3 antibody and the anti-human CD28 antibody need to be continuously present in the culture system to stimulate the amplification of the subpopulations.

The specific steps for in-vitro amplification of the CD8+ T cells and the PD-1+CD8+ T cells are as follows:

a. isolation of PBMCs: PBMCs are labeled with an anti-human CD3 antibody, an anti-human CD8 antibody and an anti-human PD-1 antibody with different fluorescent labels; and the PBMCs are stained at room temperature in the dark, and the cells are resuspended with a staining buffer, washed by centrifugation and then resuspended with the staining buffer;

b. the CD8+ T cells and the PD-1+CD8+ T cells in the peripheral blood mononuclear cells are sorted by flow cytometry;

c. the cells sorted into a 96-well plate are allowed to stand for 1 hour, and Pam3CK4 (1-300 ng/ml), FSL-1 (1-100 ng/ml), Flagellin (10-100 ng/ml), IL-7 (20 ng/ml-200 ng/ml), IL-2 (10 U/ml-100 U/ml), IL-15 (10 ng/ml-100 ng/ml) as well as magnetic beads coated with an anti-human CD3 antibody and an anti-human CD28 antibody are added, wherein the ratio of the magnetic beads to the cells is 1:1; and the cells are cultured in an incubator at 37° C. for one week; and d. the cells in the 96-well plate are transferred to a 24-well plate in the second week, and then the cells are sequentially transferred to a T25 cell culture flask, a T75 cell culture flask and a T175 cell culture flask according to the number of growing cells; and each time a culture dish is replaced, corresponding media and stimulants are supplemented until the desired number of cells is achieved.

Sources of the CD8+ T cells and other functional CD8+ T cell subpopulations include, but are not limited to, peripheral venous blood from healthy subjects, HIV-1 infected individuals or tumor patients, and also include a variety of lymphocytic leukemia, lung cancer, breast cancer, esophageal cancer, gastric cancer, liver cancer, uterine cancer, cervical cancer, renal cancer, pancreatic cancer, nasopharyngeal cancer, small intestine cancer, large intestine cancer, colorectal cancer, bladder cancer, bone cancer, prostate cancer, ovarian cancer, thyroid cancer, rhabdomyoma, leiomyoma and cerebroma, as well as HIV infection, HBV infection, HCV infection and *Mycobacterium tuberculosis* infection.

The present invention has the following beneficial effects: compared with the prior art, the present invention provides a method for amplifying of CD8+ T cells and functional cell subpopulations thereof in-vitro, wherein one or more TLR agonists, recombinant human cytokines IL-7, IL-2 and IL-15 as well as magnetic beads coated with an anti-human CD3 antibody and an anti-human CD28 antibody are used in combination, and the continuous stimulation is maintained by the above stimulants, which can significantly enhance the amplification efficiency and functional repair of the CD8+ T cells, and enable the amplification of the CD8+ T cell subpopulations (e.g. PD-1+CD8+ T cells and effector memory CD8+ T cells ($T_{EM}$)) that are difficult to amplify under conventional culture conditions so as to obtain cells that can maintain the function of the cell subpopulations; and analysis of cytokine secretion from the amplified CD8+ T cells and PD-1+CD8+ T cells show that the proportion of CD8 cells capable of secreting CD107a and IFN-γ is 93.30%, and the proportion of CD8 cells capable of secreting CD107a and Granzyme B is 90.17%, which is much higher than that seen in the prior art.

DETAILED DESCRIPTION OF THE INVENTION

The present invention provides a method for amplifying CD8+ T cells and functional cell subpopulations thereof in-vitro, wherein one or more TLR agonists, recombinant human cytokines IL-7, IL-2 and IL-15 as well as magnetic beads coated with an anti-human CD3 antibody and an anti-human CD28 antibody are used in combination, and the continuous stimulation is maintained by the above stimulants, which can significantly enhance the amplification efficiency and activation of the CD8+ T cells, and enable the amplification of the CD8+ T cell subpopulations (e.g. PD-1+ CD8+ T cells and effector memory CD8+ T cells ($T_{EM}$)) that are difficult to amplify under conventional culture conditions so as to obtain cells that can maintain the function of the cell subpopulations.

In the present invention, the stimulants for stimulating the CD8+ T cells include TLR1/2 agonists, TLR2/6 agonists and TLR5 agonists, recombinant human cytokines IL-7, IL-2 and IL-15 as well as magnetic beads coated with an anti-human CD3 antibody and an anti-human CD28 antibody. Sources of the CD8+ T cells and the PD-1+CD8+ T cells as well as other functional CD8+ T cell subpopulations include, but are not limited to, peripheral blood from healthy subjects, HIV-1 infected individuals or tumor patients. This amplification technique is also applicable to CD8+ T cells and other functional CD8+ T cell subpopulations obtained by other isolation methods, e.g. sorted and purified CD137+ CD8+ T cells, sorted and purified CD160+CD8+ T cells, sorted and purified naive CD8+ T cells ($T_{naive}$), sorted and purified central memory CD8+ T cells ($T_{CM}$), sorted and purified effector memory CD8+ T cells ($T_{EM}$), sorted and purified effector CD8+ T cells ($T_{EMRA}$), sorted and purified transitional memory CD8+ T cells (TIM), sorted and purified effector stem cell CXCR5+CD8+ T cells, and sorted and purified tissue-resident memory CD8+ T cells ($T_{RM}$).

In order that those skilled in the art better understand the technical solution of the present invention, the present invention will be further described below in detail with reference to specific examples.

Example 1: Isolation of Peripheral Blood Mononuclear Cells 1. 20 ml of human peripheral blood anticoagulated by heparin was placed in a centrifuge tube. The peripheral blood was diluted with normal saline in a ratio of 1:1 and evenly mixed.

2. 15 ml of a lymphocyte isolation solution (Ficoll) was added to a new 50 mL centrifuge tube, then the evenly mixed blood dilution solution was slowly added to the upper layer of the lymphocyte isolation solution along the tube wall in a volume ratio of the Ficoll to the blood dilution solution of 1:2 to form a clear separation therebetween, and the resulting solution was centrifuged at 3000 rpm for 30 min.

3. After centrifugation was completed, a mononuclear cell layer was transferred into a new 50 ml centrifuge tube and washed once with 30 ml of an X-VIVO-15 medium, centrifuged at 800 g for 5 min, and the supernatant was discarded.

4. 20 ml of the X-VIVO-15 medium was added, the resulting mixture was evenly mixed by blowing and suction, centrifuged at 200 g at room temperature for 10 min, and the supernatant was discarded. 10 ml of the X-VIVO-15 medium was added for resuspending and counting.

Example 2: Proliferation of CD8+ T Cells was Effectively Stimulated by TLR Agonists 1. Peripheral blood mononuclear cells (PBMC) of healthy subjects were isolated according to Example 1.

2. CD8+ T cells were sorted using an EasySep™ Negative Selection Human CD8+ T cell Enrichment kit (Stemcell: 19053).

3. The sorted CD8 cells were stained using Cell Proliferation Dye eFluor 670 (ebioscience: 65-0840-90).

4. The cells were placed in a 96-well U-shaped bottom plate with 1×10⁵ cells per well.

5. The following stimulants and TLR agonists (invivoGen: tlr-kit1hw, human TLR1-9 Agonist KIT) were added in groups:

(1) blank control;
(2) anti-human CD3 antibody;
(3) anti-human CD3 antibody+anti-human CD28 antibody;

(4) anti-human CD3 antibody+TLR1/2 agonist-Pam3CSK4 (0.1-1 µg/ml);

(5) anti-human CD3 antibody+TLR2 agonist-HKLM ($10^8$ cells/ml);

(6) anti-human CD3 antibody+TLR3 agonist-Poly(I:C) (10 ng-10 ug/ml);

(7) anti-human CD3 antibody+TLR3 agonist-Poly(I:C) LMW (30 ng-10 ug/ml);

(8) anti-human CD3 antibody+TLR4 agonist-*E. coli* K12 LPS (10 ng-10 µg/ml);

(9) anti-human CD3 antibody+TLR5 agonist-*S. typhimurium* Flagellin (10 ng-10 µg/ml);

(10) anti-human CD3 antibody+TLR6/2 agonist-FSL-1 (1 ng-1 µg/ml);

(11) anti-human CD3 antibody+TLR7 agonist-Imiquimod (0.25-10 ug/ml);

(12) anti-human CD3 antibody+TLR8 agonist-ssRNA40 (0.25-10 ug/ml); and (13) anti-human CD3 antibody+TLR9 agonist-ODN2006 (5 µM).

(The anti-human CD3 antibody and the anti-human CD28 antibody used were magnetic beads coated with the antibodies (CELLection Pan Mouse IgG Kit, Invitrogen: 11531D), wherein the ratio of the cells to the magnetic beads was 1:1)

6. The cells were cultured in the 96-well U-shaped bottom plate, and cultured in a cell incubator for 7 days.

Figure 1:
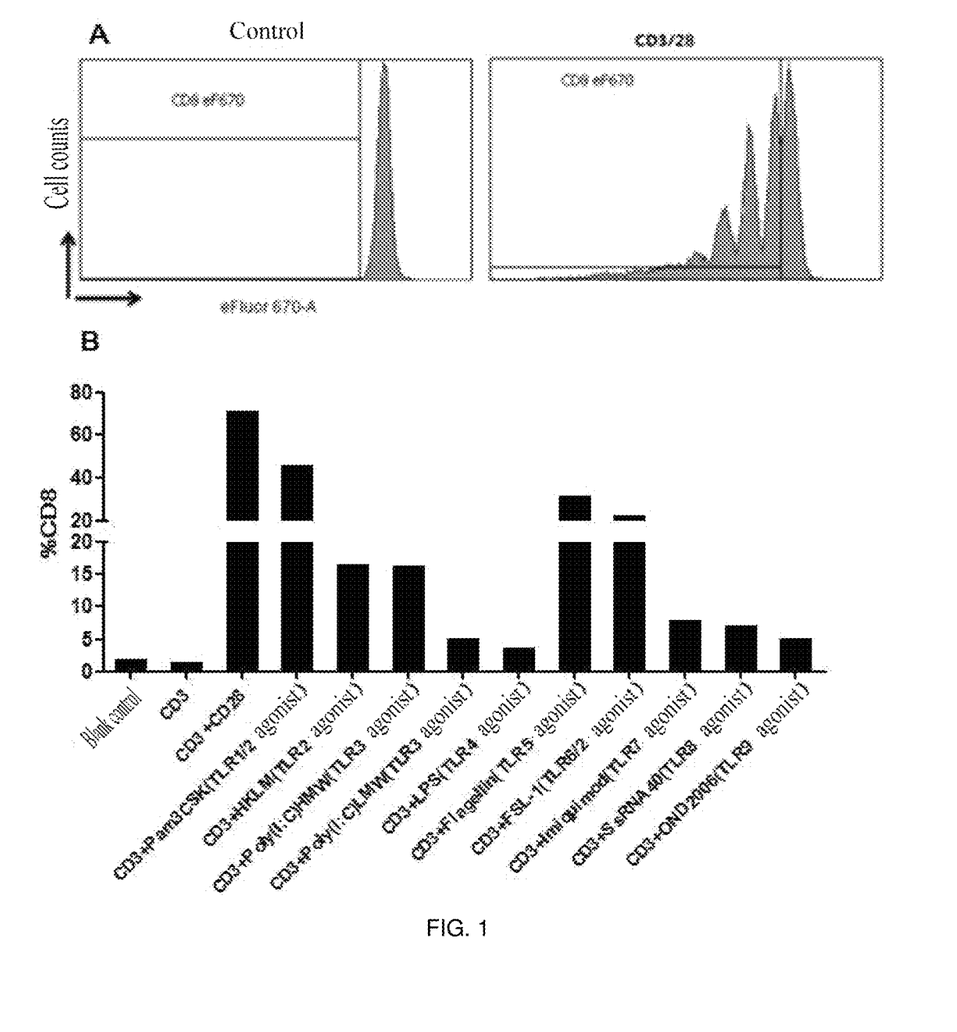
FIG. 1 is a schematic view showing the proliferation of CD8+ T cells of healthy subjects stimulated by TLR agonists; wherein panel A is a diagram showing the proliferation of CD8 cells under the conditions of blank control as well as an anti-human CD3 antibody and an anti-human CD28 antibody as detected by flow cytometry; and panel B shows the proportion of proliferating CD8 cells in the total number of CD8+ T cells under different stimulation conditions, and the higher proportion stands for the stronger proliferation ability.

7. The proliferation of the CD8+ T cells was detected by a flow cytometer under the stimulation conditions of different TLR agonists. FIG. 1A is a diagram showing the proliferation of CD8 cells under the conditions of blank control (left panel) as well as an anti-human CD3 antibody and an anti-human CD28 antibody (right panel). FIG. 1B is a statistical chart showing the proliferation proportion of CD8 cells under different stimulation conditions. The results showed that compared with cell proliferation stimulated by magnetic beads coated with an anti-human CD3 antibody alone, the proliferation of CD8+ T cells could be effectively stimulated by a TLR1/2 agonist (Pam3CK4), a TLR2/6 agonist (FSL-1) or a TLR5 agonist (Flagellin) in combination with an anti-human CD3 antibody.

Example 3: Proliferation of CD8+ T Cell Subpopulations was Effectively Stimulated by TLR Agonists TLR agonists were capable of effectively stimulating the proliferation of CD8+ T cell subpopulations, i.e. central memory T cells ($T_{CM}$) and effector memory T cells ($T_{EM}$).

1. Peripheral blood mononuclear cells (PBMC) of healthy subjects were isolated.

2. CD8+ T cells were sorted using an EasySep™ Negative Selection Human CD8+ T cell Enrichment kit (stem cell: 19053).

3. The sorted CD8 cells were stained using Cell Proliferation Dye eFluor 670 (ebioscience: 65-0840-90).

4. The cells were placed in a 96-well U-shaped bottom plate with $1\times10^5$ cells per well.

5. The following stimulants and TLR agonists (invivoGen: tlr-kit1hw, human TLR1-9 Agonist KIT) were added in groups:

(1) anti-human CD3 antibody;

(2) anti-human CD3 antibody+TLR1/2 agonist-Pam3CSK4 (0.1-1 µg/ml);

(3) anti-human CD3 antibody+TLR6/2 agonist-FSL-1 (1 ng-1 µg/ml); and (4) anti-human CD3 antibody+TLR5 agonist-*S. typhimurium* Flagellin (10 ng-10 µg/ml).

(The anti-human CD3 antibody used was magnetic beads coated with the antibody (CELLection Pan Mouse IgG Kit, Invitrogen: 11531D), wherein the ratio of the cells to the magnetic beads was 1:1)

6. The cells were cultured in the 96-well U-shaped bottom plate, and cultured in a cell incubator for 7 days.

7. The cells were labeled with antibodies CD8 (BD: 561423), CD45RA (eBioscience: 25-0458-42) and CCR7 (eBioscience: 17-1979-42), and the influence of different TLR agonists on the proliferation of CD8+ T subpopulations ($T_{Naive}$: Naive T cells, $T_{CM}$: central memory T cells, $T_{EM}$: effector memory T cells) was detected by flow cytometry.

Figure 2:
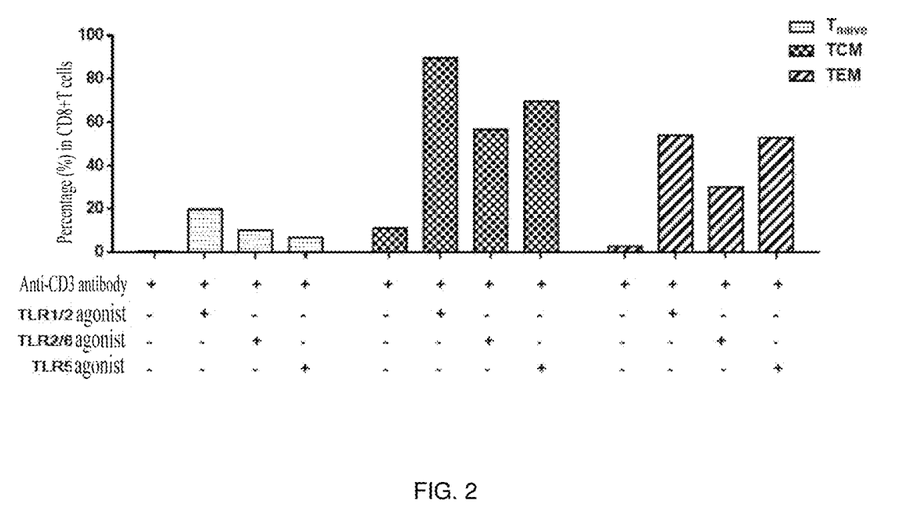
FIG. 2 is a schematic view showing the proliferation of CD8+ T cell subpopulations $T_{CM}$ and $T_{EM}$ of healthy subjects stimulated by TLR agonists; wherein the ordinate shows the proportion of proliferating CD8 cells in the total number of CD8+ T cells, and the higher proportion stands for the stronger proliferation ability. $T_{Naive}$: Naive T cells, $T_{CM}$: central memory T cells, and $T_{EM}$: effector memory T cells.

8. The results showed that compared with cell proliferation stimulated by magnetic beads coated with an anti-human CD3 antibody alone, the proliferation of central memory CD8+ T cells ($T_{CM}$) and effector memory T cells ($T_{EM}$) could be effectively stimulated by a TLR1/2 agonist (Pam3CK4), a TLR2/6 agonist (FSL-1) or a TLR5 agonist (Flagellin) in combination with an anti-human CD3 antibody (as shown in FIG. 2).

Example 4: Proliferation of CD8+ T Cell Subpopulations of HIV-1 Infected Individuals was Stimulated by TLR Agonists TLR agonists were capable of effectively stimulating the proliferation of CD8+ T cell subpopulations, i.e. central memory T cells ($T_{CM}$) and effector memory T cells ($T_{EM}$) of HIV-1 infected individuals.

1. Peripheral blood mononuclear cells (PBMC) of HIV-1 infected individuals were isolated.

2. CD8+ T cells were sorted using an EasySep™ Negative Selection Human CD8+ T cell Enrichment kit (Stemcell: 19053).

3. The sorted CD8 cells were stained using Cell Proliferation Dye eFluor 670 (ebioscience: 65-0840-90).

4. The cells were placed in a 96-well U-shaped bottom plate with $1\times10^5$ cells per well.

5. The following stimulants and TLR agonists (invivoGen: tlr-kit1hw, human TLR1-9 Agonist KIT) were added in groups:

(1) anti-human CD3 antibody;

(2) anti-human CD3 antibody+TLR1/2 agonist-Pam3CSK4 (0.1-1 µg/ml);

(3) anti-human CD3 antibody+TLR6/2 agonist-FSL-1 (1 ng-1 µg/ml);

(4) anti-human CD3 antibody+TLR5 agonist-*S. typhimurium* Flagellin (10 ng-10 µg/ml);

(5) anti-human CD3/28 antibodies;

(6) anti-human CD3/28 antibodies+TLR1/2 agonist-Pam3CSK4 (0.1-1 µg/ml);

(7) anti-human CD3/28 antibodies+TLR6/2 agonist-FSL-1 (1 ng-1 µg/ml); and (8) anti-human CD3/28 antibodies+TLR5 agonist-*S. typhimurium* Flagellin (10 ng-10 µg/ml).

(The anti-human CD3 antibody and the anti-human CD28 antibody in the form of coated magnetic beads (CELLection Pan Mouse IgG Kit, Invitrogen: 11531D) were used to stimulate the cells, wherein the ratio of the cells to the magnetic beads was 1:1)

6. The cells were cultured in the 96-well U-shaped bottom plate, and cultured in a cell incubator for 7 days.

7. The cells were labeled with antibodies CD8 (BD: 561423), CD45RA (eBioscience: 25-0458-42) and CCR7 (eBioscience: 17-1979-42), and the influence of different TLR agonists on the proliferation of CD8+ T subpopulations ($T_{Naive}$: Naive T cells, $T_{CM}$: central memory T cells, $T_{EM}$: effector memory T cells) was detected by a flow cytometer.

Figure 3:
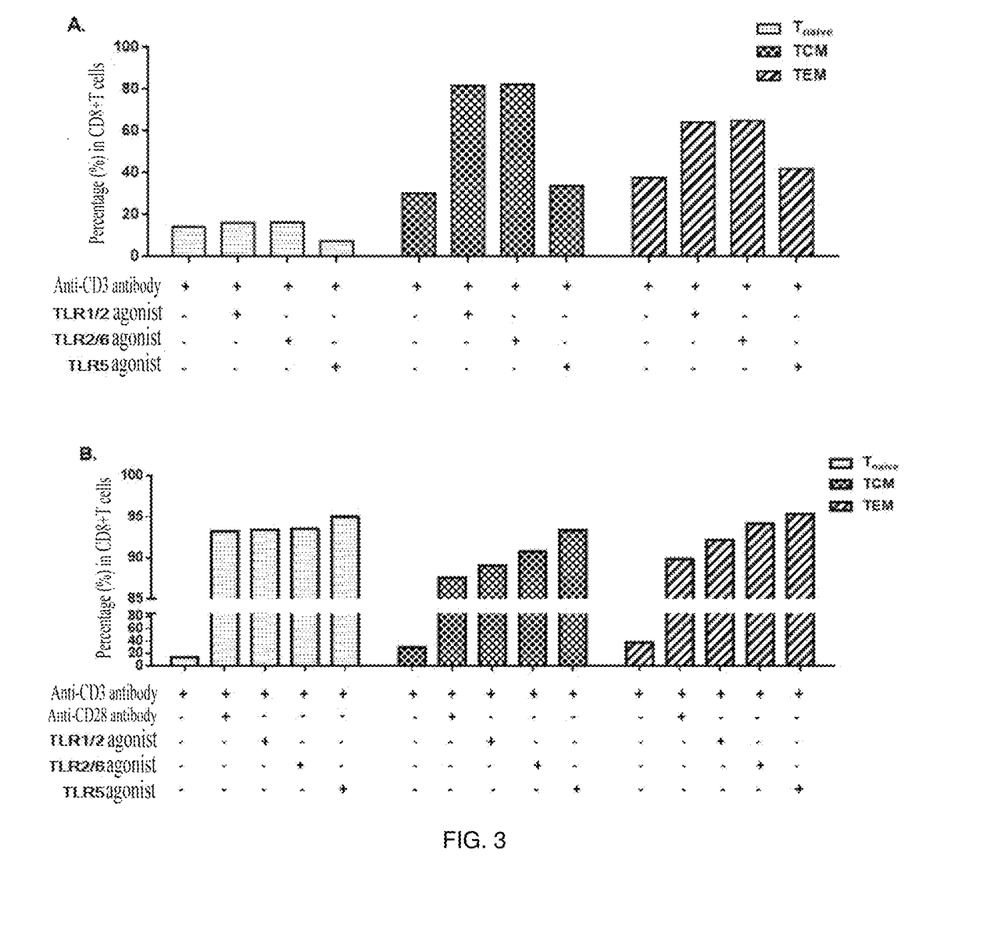
FIG. 3 is a schematic view showing the proliferation of CD8+ T cell subpopulations $T_{CM}$ and $T_{EM}$ of HIV-1 infected individuals stimulated by TLR agonists; wherein panel A shows the comparison between the proliferation stimulated by an anti-human CD3 antibody and the combination with different TLR agonists; panel B shows the comparison among the proliferation stimulated by an anti-human CD3 antibody, anti-human CD3/28 antibodies, and anti-human CD3/CD28 antibodies in combination with different TLR agonists; and the ordinates in panels A and B represent the proportion of proliferating CD8 cells in the total number of CD8+ T cells, and the higher proportion stands for the stronger proliferation ability.

8. The results showed that compared with cell proliferation stimulated by magnetic beads coated with an anti-human CD3 antibody alone, the proliferation of central memory CD8+ T cells ($T_{CM}$) and effector memory T cells ($T_{EM}$) could be more effectively stimulated by adding a TLR1/2 agonist (Pam3CK4), a TLR2/6 agonist (FSL-1) or a TLR5 agonist (Flagellin) (as shown in FIG. 3A); and compared with cell proliferation stimulated by magnetic beads coated with anti-human CD3/28 antibodies, the proliferation of central memory CD8+ T cells ($T_{CM}$) and effector memory T cells ($T_{EM}$) could also be further enhanced by adding a TLR1/2 agonist (Pam3CK4), a TLR2/6 agonist (FSL-1) or a TLR5 agonist (Flagellin) (as shown in FIG. 3B).

Example 5: Sorting of CD8+ T Cells and PD-1+CD8+ T Cells

1. Peripheral blood mononuclear cells (PBMC) of healthy subjects were isolated according to Example 1.
2. $1 \times 10^7$ isolated PBMCs were taken and labeled with an anti-human CD3 antibody, an anti-human CD8 antibody and an anti-human PD-1 antibody with different fluorescent labels.
3. The PBMCs were stained at room temperature in the dark for 20 min, and the cells were resuspended with a staining buffer (1×PBS+2% FBS), centrifuged at 500 G for 5 min, washed twice and then resuspended with the staining buffer to a concentration of $1 \times 10^7$ cells/ml.
4. CD3+CD8+ T cells and CD3+CD8+PD-1+ T cells were sorted by a flow cytometer into a 96-well plate, and 100 µl of an X-VIVO15 medium was preliminarily placed in the 96-well plate. $1-3 \times 10^4$ cells were sorted per well.

Example 6: TLR Agonists were Capable of Effectively Enhancing the Proliferation of PD-1+CD8+ T Cells Stimulated by Anti-Human CD3/CD28 Antibodies 1. Peripheral blood mononuclear cells (PBMC) of healthy subjects were isolated.
2. $1 \times 10^7$ PBMCs were taken, and an anti-human CD3 antibody (BD: 558117), a CD8 antibody (BD: 561423) and a PD-1 antibody (BD: 565024) were added. The cells were incubated at room temperature in the dark for 20 min, then washed once with 500 g of PBS for 5 min and then resuspended with 1 ml of PBS.
3. CD3+CD8+PD-1+ T cells were sorted into a 96-well U-shaped bottom plate using a flow cell sorter (BD FACSAria II), with 6,000 cells sorted per well. The cells sorted into the 96-well plate were allowed to stand for 1 hr, and fresh X-VIVO15 medium was added.
4. The following TLR agonists (invivoGen: tlr-kit1hw, human TLR1-9 Agonist KIT) were added in groups: a TLR1/2 agonist-Pam3CSK4 (0.1-1 µg/ml), a TLR5 agonist-S. typhimurium Flagellin (10 ng-10 µg/ml) and a TLR6/2 agonist-FSL-1 (1 ng-1 µg/ml) in combination with cytokines IL-7 (PeproTech: 200-07-1000, 20 ng/ml-200 ng/ml) and IL-15 (PeproTech:200-15-1000, 10 ng/ml-100 ng/ml) as well as magnetic beads (CELLection™ Dynabeads, Invitrogen: 11531D) co-coated with an anti-human CD3 antibody (BD: 555336) and an anti-human CD28 antibody (BD: 555725).

The following stimulants were added in groups to 5 wells:
(1) CD3/28+IL-7+IL-15+TLR1/2 agonist+TLR2/6 agonist+TLR5 agonist;
(2) CD3/28+IL-7+IL-15+TLR1/2 agonist+TLR2/6 agonist;
(3) CD3/28+IL-7+IL-15+TLR1/2 agonist+TLR5 agonist;
(4) CD3/28+IL-7+IL-15++TLR2/6 agonist+TLR5 agonist; and
(5) CD3/28+IL-7+IL-15.

5. The cells were cultured in an incubator at 37° C., transferred to a 24-well culture plate on the $8^{th}$ day and transferred to a T25 cell culture flask on the $15^{th}$ day. Each time a culture flask was replaced, magnetic beads coated with CD3/28 were supplemented to the cells, wherein the ratio of the magnetic beads to the cells was 1:1. The cells were counted each time the medium was replaced.

Figure 4:
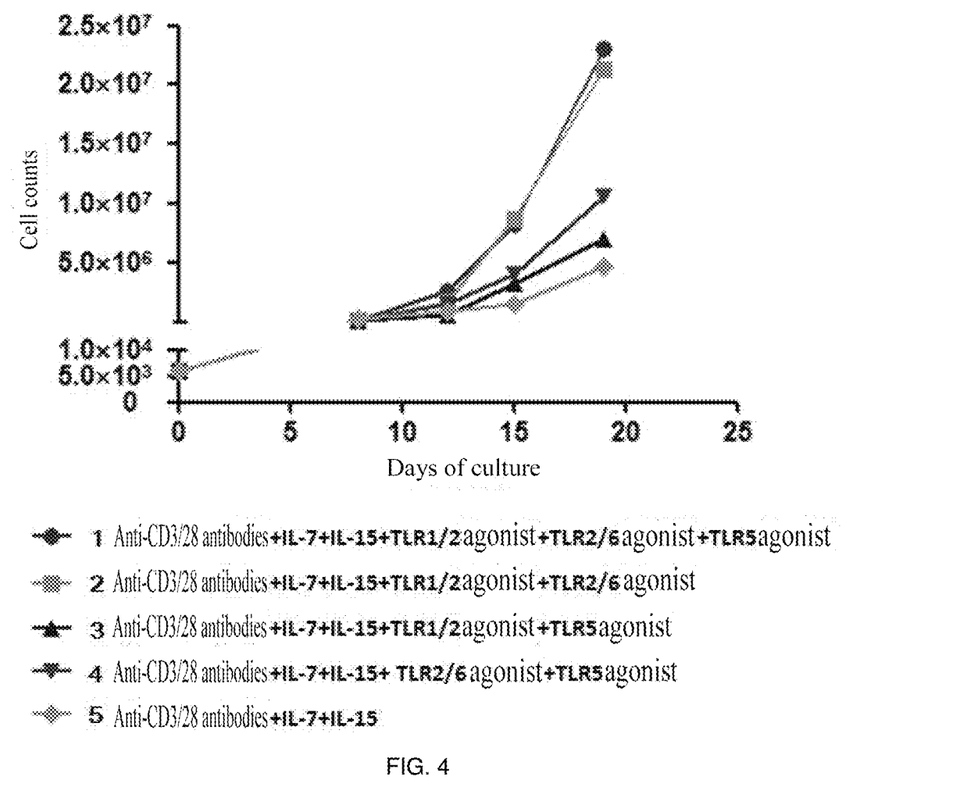
FIG. 4 shows cell proliferation curves of sorted PD-1+ CD8+ T cells of healthy subjects in different culture systems.

6. After culture for 19 days, it was observed that PD-1+CD8+ T cells proliferated at the fastest rate under the culture conditions of CD3/28+IL-7+IL-15+TLR1/2 agonist+TLR2/6 agonist+TLR5 agonist. The experimental results are shown in FIG. 4.

Example 7: Amplification of CD8+ T Cells and PD-1+CD8+ T Cells

1. The cells sorted into the 96-well plate were allowed to stand for 1 hr, and fresh X-VIVO 15 medium was added. A TLR1/2 agonist (Pam3CK4, invivoGen: tlrl-pms, 1-300 ng/ml), a TLR2/6 agonist (FSL-1, invivoGen: tlrl-fsl, 1-100 ng/ml), a TLR5 agonist (Flagellin, invivoGen: tlrl-epstfla-5, 10-100 ng/ml), IL-7 (PeproTech: 200-07-1000, 20 ng/ml-200 ng/ml), IL-2 (PeproTech: 200-02-1000, 10 U/ml-100 U/ml), IL-15 (PeproTech: 200-15-1000, 10 ng/ml-100 ng/ml) as well as magnetic beads (CELLection™ Dynabeads, Invitrogen: 11531D) coated with an anti-human CD3 antibody (BD: 555336) and an anti-human CD28 antibody (BD: 555725) were added at the same time, wherein the ratio of the magnetic beads to the cells was 1:1. The cells were placed in an incubator at 37° C. for one week.

2. The cells in the 96-well plate were transferred to a 24-well plate in the second week, and then the cells were sequentially transferred to a T25 cell culture flask, a T75 cell culture flask and a T175 cell culture flask according to the number of growing cells.

Figure 5:
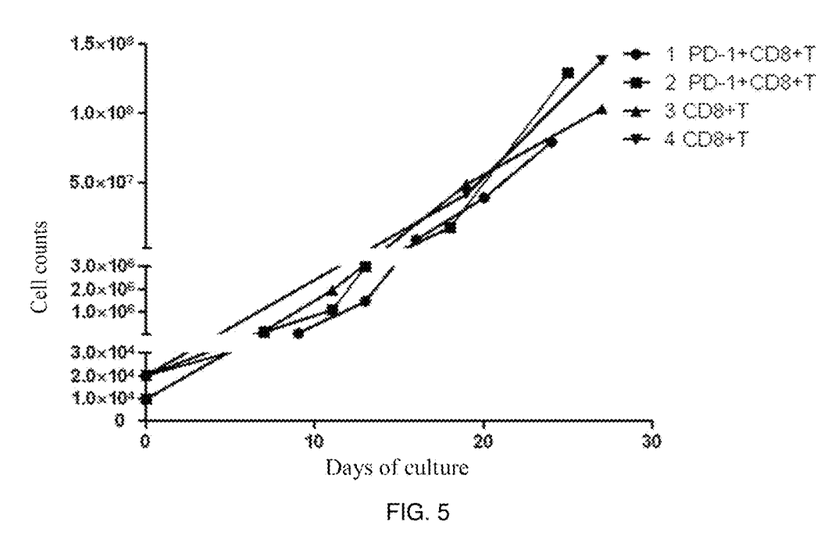
FIG. 5 shows proliferation curves of PD-1+CD8+ T cells and CD8+ T cells stimulated by TLR agonists in combination with cytokines and anti-human CD3/28 antibodies.

3. Each time a culture dish was replaced, corresponding media and stimulants were supplemented until the desired number of cells was achieved. Cell proliferation is shown in FIG. 5 illustrating proliferation curves of PD-1+CD8+ T cells of two persons and proliferation curves of CD8+ T cells of two persons. The number of cells amplified could reach 10,000 times or even 100,000 times.

Figure 6:
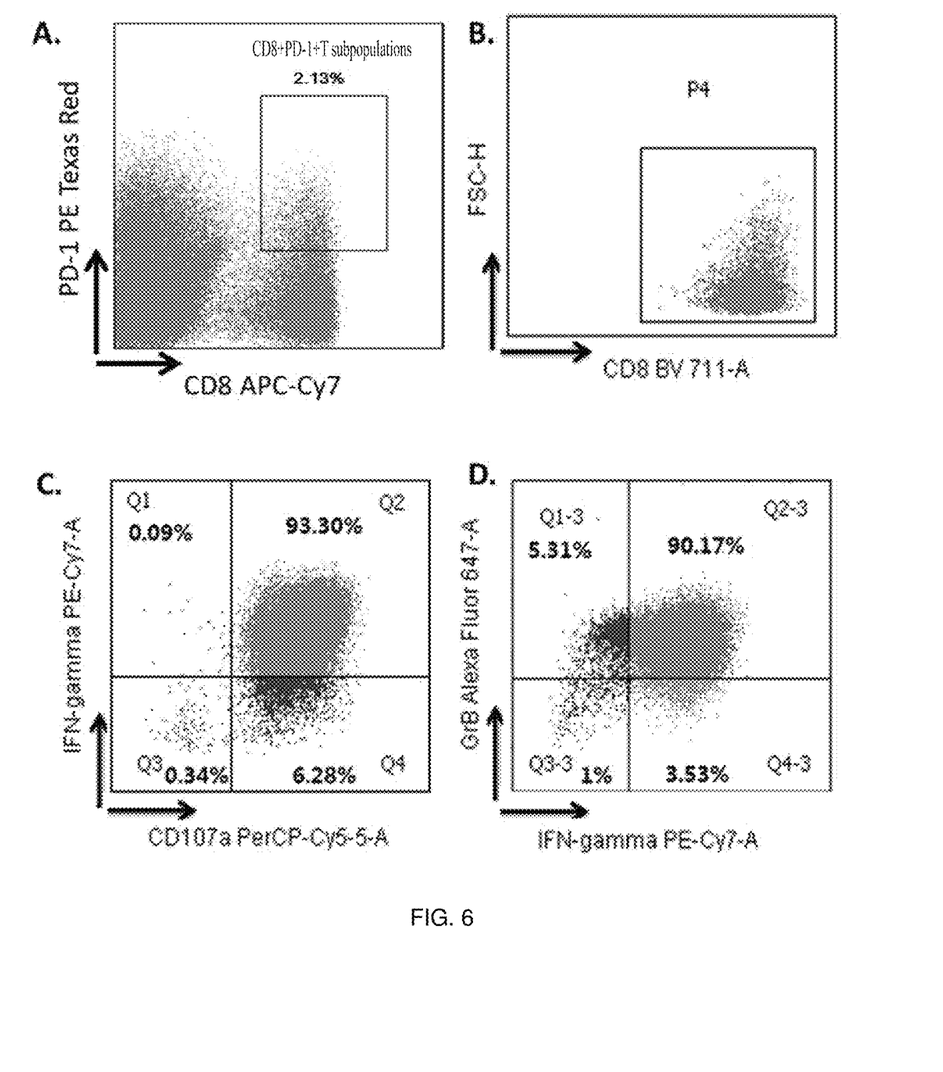
FIG. 6 shows the detection of the ability of sorted PD-1+CD8+ T cells that are proliferated in vitro to secrete IFN-γ, Granzyme B and CD107a; wherein A is a schematic view of PD-1+CD8+ cells sorted from PBMCs; B is a schematic view of stained CD8+ T cells in the amplified product; C is a schematic view showing the detection of the ability of the amplified product to secrete IFN-γ and CD107a; and D is a schematic view showing the ability of the amplified product to secrete IFN-γ and Granzyme B.

Example 8: Detection of Cytokine Secretion Ability of Amplified CD8+ T Cells and PD-1+CD8+ T Cells The cells amplified in Example 7 were taken and placed in a 96-well plate at 1×106 cells/well. PMA (phorbol myristoyl acetate) (50 ng/ml)/ionomycin (5 µM) and an anti-CD107a antibody (Biolegend: 328616) were added. After 1 hr, GolgiPlug (BD: 555029) was added, and cultured for 5 hrs, and then the cells were stained with IFN-γ (BD: 557763) and Granzyme B (abbreviated as GrB in FIG. 6, (BD: 560212)). The expression of CD107a, IFN-γ and GranzymeB in the cells was detected by flow cytometry, and the results were shown in FIG. 6, wherein the proportion of CD8 cells capable of secreting CD107a and IFN-γ was 93.30%, and the proportion of CD8 cells capable of secreting IFN-γ and Granzyme B was 90.17%.

Example 9: Culture Supernatants of Amplified CD8+ T Cells and PD-1+CD8+ T Cells were Analyzed for *Mycoplasma* and Endotoxin Culture supernatants of the amplified CD8+ T cells and PD-1+CD8+ T cells were analyzed for *mycoplasma* using a LONZA kit (MycoAlert *Mycoplasma* DetectionKIT) according to the manufacturer's instructions. The ratio of the detected value B to the detected value A of a microplate reader was calculated. If the ratio was less than 0.9, the result was qualified as valid and there was no *mycoplasma* contamination. If the ratio was greater than or equal to 0.9, the detection result was disqualified. The ratio in this experiment was less than 0.9, i.e. the amplified CD8+ T cells and PD-1+CD8+ T cells had no *mycoplasma* contamination.

Culture supernatants of the amplified CD8+ T cells and PD-1+CD8+ T cells were analyzed for endotoxin using a LONZA kit (Limulus Amebocyte Lysate QCL-1000 kit) according to the manufacturer's instructions. The endotoxin content of the sample was calculated according to a standard curve using endotoxin in *E. coli* O111:B4 as a standard. The detection result was qualified if the endotoxin content was not more than 0.3 EU/ml, but disqualified if the endotoxin content was greater than 0.3 EU/ml. The endotoxin content detected in this experiment was not more than 0.3 EU/ml, i.e. the amplified CD8+ T cells and PD-1+CD8+ T cells were qualified.

Example 10: Comparison of Proliferation of PD-1+CD8+ T Cells Under Intermittent Stimulation and Continuous Stimulation PD-1+CD8+ T cells exhibited different proliferation ability and different number of functional cells under intermittent stimulation and continuous stimulation.

Figure 7:
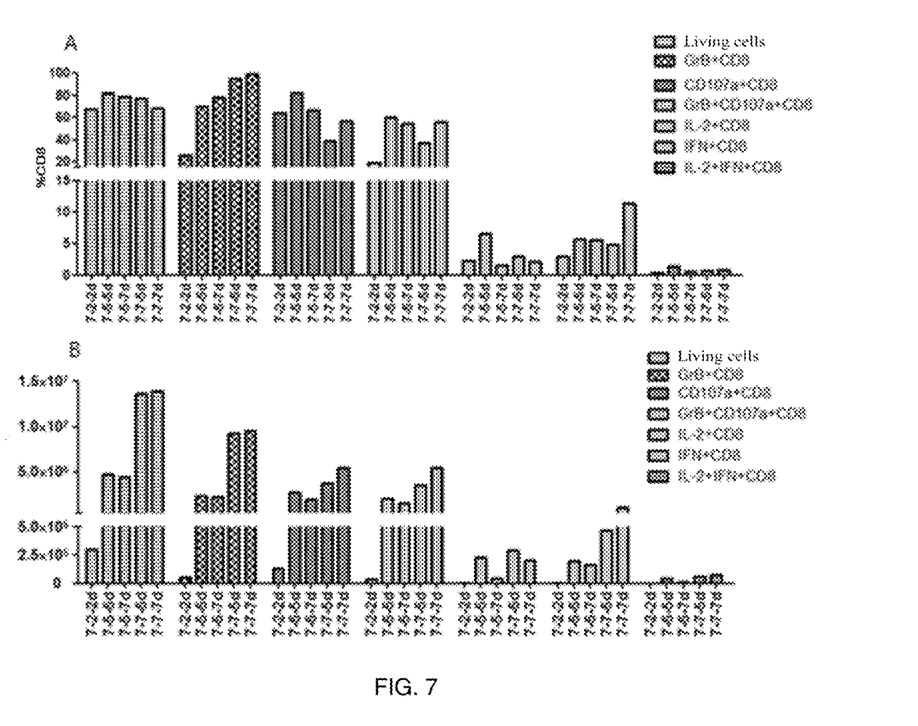
FIG. 7 is a schematic view showing the cell proliferation and function detection of PD-1+CD8+ T cells cultured for 21 days under intermittent stimulation and continuous stimulation; wherein panel A shows the proportion of cells of each population in CD8 cells in different groups, panel B shows the absolute number of cells of each population in different groups; and the description of the grouping is shown in Table 1 of Example 10.

1. Peripheral blood mononuclear cells (PBMC) of healthy subjects were isolated.
2. $1 \times 10^7$ PBMCs were taken, and an anti-human CD3 antibody (BD: 558117), a CD8 antibody (BD: 561423) and a PD-1 antibody (BD: 565024) were added. The cells were incubated at room temperature in the dark for 20 min, then washed once with 500 g of PBS for 5 min and then resuspended with 1 ml of PBS.
3. CD3+CD8+PD-1+ T cells were sorted into a 96-well U-shaped bottom plate by a flow cell sorter (BD FACSAria II), with 10,000 cells per well. The cells sorted into the 96-well plate were allowed to stand for 1 hr, and fresh X-VIVO 15 medium was added.
4. The following stimulants were used: a TLR1/2 agonist (Pam3CK4, invivoGen: tlrl-pms, 1-300 ng/ml), a TLR2/6 agonist (FSL-1, invivoGen: tlrl-fsl, 1-100 ng/ml), a TLR5 agonist (Flagellin, invivoGen: tlrl-epstfla-5, 10-100 ng/ml), IL-7 (PeproTech: 200-07-1000, 20 ng/ml-200 ng/ml), IL-2 (PeproTech: 200-02-1000, 10 U/ml-100 U/ml), IL-15 (PeproTech: 200-15-1000, 10 ng/ml-100 ng/ml) as well as magnetic beads (CELLection™ Dynabeads, Invitrogen: 11531 D) coated with an anti-human CD3 antibody (BD: 555336) and an anti-human CD28 antibody (BD: 555725). The cells were divided into 5 groups, as shown in Table 1. Taking group 7-2-2 as an example: all the stimulants were added for 7 days of continuous stimulation in the first round, the cells were transferred to a 24-well plate, all the stimulants were added for 2 days of stimulation, then the magnetic beads coated with CD3/28 were removed, the cells were cultured for 5 days and then transferred to a T25 culture flask, all the stimulants and the magnetic beads coated with anti-human CD3/28 were added for 2 days of stimulation, then the magnetic beads coated with CD3/28 were removed, and the cells continued to be cultured for 5 days. The days of stimulation and intermittent days are shown in Table 1.

TABLE 1

| | cell culture | | | | | |
| --- | --- | --- | --- | --- | --- | --- |
| | First round of culture | | Second round of culture | | Third round of culture | |
| Group | Days of stimulation | Intermittent days | Days of stimulation | Intermittent days | Days of stimulation | Intermittent days |
| 7-2-2 | 7 | 0 | 2 | 5 | 2 | 5 |
| 7-5-5 | 7 | 0 | 5 | 2 | 5 | 2 |
| 7-5-7 | 7 | 0 | 5 | 2 | 7 | 0 |
| 7-7-5 | 7 | 0 | 7 | 0 | 5 | 2 |
| 7-7-7 | 7 | 0 | 7 | 0 | 7 | 0 |

5. After the three rounds of culture and stimulation, the 5 groups of cells were respectively taken and placed in a 96-well plate at $1 \times 10^6$ cells/well. $1 \times 10^6$ magnetic beads coated with an anti-human CD3 antibody and an anti-human CD28 antibody, and 5 μl of an anti-CD107a antibody (Biolegend: 328616) were added to 100 ul of the system. After 1 hr, GolgiPlug (BD: 555029) was added, and cultured for 5 hrs, then the cells were stained with CD8 (BD: 563677), IFN-γ (Biolegend: 502506), IL-2 (Biolegend: 500307) and Granzyme B (abbreviated as GrB in FIG. 7, BD: 560212), and the expressions of CD107a, IFN-γ, IL-2 and Granzyme B in the cells were detected by flow cytometry.
6. The cells of each group were counted, and the proportion and count of different functional cells in each group of cells were calculated. The results are shown in FIG. 7. The cells in Group 7-7-7, i.e. the continuous stimulation group, proliferate faster, and a higher proportion of cells were shown to secrete CD107a, IFN-γ, IL-2 and Granzyme B, i.e. continuous stimulation by an anti-human CD3 antibody and an anti-human CD28 antibody is the most effective way to amplify PD-1+CD8+ T cells and maintain the function of the cell subpopulations.

Example 11: Proliferation of PD-1+CD8+ T Cells of Lung Cancer Patients was Stimulated by TLR Agonists 1. Peripheral blood mononuclear cells (PBMC) of lung cancer patients were isolated.
2. $1 \times 10^7$ PBMCs were taken, and an anti-human CD3 antibody (BD: 558117), a CD8 antibody (BD: 561423) and a PD-1 antibody (BD: 565024) were added. The cells were incubated at room temperature in the dark for 20 min, then washed once with 500 g of PBS for 5 min and then resuspended with 1 ml of PBS.
3. CD3+CD8+PD-1+ T cells were sorted into a 96-well U-shaped bottom plate by a flow cell sorter (BD FACSAria II), and 12,000 cells were sorted. The cells sorted into the 96-well plate were allowed to stand for 1 hr, and fresh X-VIVO 15 medium was added.
4. The following TLR agonists were added to the X-VIVO medium: a TLR1/2 agonist (Pam3CK4, invivoGen: tlrl-pms, 1-300 ng/ml), a TLR2/6 agonist (FSL-1, invivoGen: tlrl-fsl, 1-100 ng/ml), a TLR5 agonist (Flagellin, invivoGen: tlrlepstfla-5, 10-100 ng/ml), IL-7 (PeproTech: 200-07-1000, 20 ng/ml-200 ng/ml), IL-2 (PeproTech: 200-02-1000, 10 U/ml-100 U/ml), IL-15 (PeproTech: 200-15-1000, 10 ng/ml-100 ng/ml) as well as magnetic beads (CELLection™ Dynabeads, Invitrogen: 11531 D) coated with an anti-human CD3 antibody (BD: 555336) and an anti-human CD28 antibody (BD: 555725), wherein the ratio of the magnetic beads to the cells was 1:1.

5. The cells in the 96-well plate were transferred to a 24-well plate in the second week according to cell growth, and then the cells were sequentially transferred to a T25 cell culture flask, a T75 cell culture flask and a T175 cell culture flask according to the number of growing cells.

Figure 8:
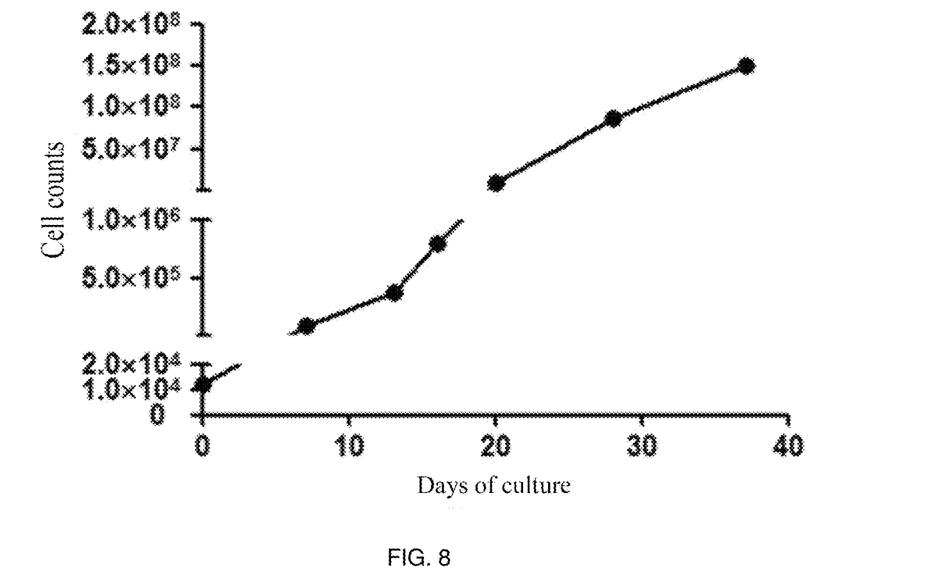
FIG. 8 shows an amplification curve of PD-1+CD8+ T cells of lung cancer patients.

6. The cells were counted during cell culture. The amplification curve is shown in FIG. 8: the sorted PD-1+CD8+ T cells are amplified to $1.51 \times 10^8$ cells from initially 12,000 cells after more than 30 days of in-vitro stimulation, and the number is amplified by 12583 times.

The basic principles, main features and advantages of the present invention have been illustrated and described above. Those skilled in the art should understand that the present invention is not limited to the above examples, merely the principles of the present invention are described in the above examples and the description, various changes and improvements can also be made to the present invention without departing from the spirit and scope of the present invention, and these changes and improvements shall fall within the claimed scope of the present invention. The claimed scope of the present invention is defined by the appended claims and equivalents thereof.

The invention claimed is:

1. A method for inducing in-vitro amplification of PD-1+CD8+T cell subpopulations, comprising adding anti-human CD3 antibody, anti-human CD28 antibody, cytokine IL-7, cytokine IL-15, and a Toll-like receptor agonist chosen from one or more in the group of TLR1/2 agonists, TLR2/6 agonists and TLR5 agonists, to a culture system for the PD-1+CD8+T cell subpopulations, thereby causing the in-vitro amplification and functional repair of the PD-1+CD8+T cell subpopulations thereof.

2. The method according to claim 1, wherein the TLR1/2 agonists comprise Pam3CK4; the TLR2/6 agonists comprise FSL-1, Pam2CGDPKHPKSF, or a combination thereof; and the TLR5 agonists comprise Flagellin.

3. The method according to claim 1, wherein the anti-human CD3 antibody or the anti-human CD28 antibody is coated on magnetic beads.

4. The method according to claim 1, wherein the PD-1+CD8+T cell subpopulations comprise sorted and purified PD-1+CD8+T cells.

5. The method according to claim 4, wherein when the PD-1+CD8+T cell subpopulations are amplified in vitro, the anti-human CD3 antibody and the anti-human CD28 antibody are continuously present in the culture system to continuously stimulate the amplification of the PD-1+CD8+T cell subpopulations.

6. The method according to claim 1, wherein the in-vitro amplification of the PD-1+CD8+T cell subpopulations comprise:
   a. isolation of peripheral blood mononuclear cells (PBMCs) by labeling PBMCs with an anti-human CD3 antibody, an anti-human CD8 antibody and an anti-human PD-1 antibody with different fluorescent labels; staining the PBMCs at room temperature in the dark, resuspending the cells with a staining buffer, washing the cells by centrifugation and then resuspending the cells with the staining buffer;
   b. sorting the CD3+CD8+PD-1+T cells by a flow cytometer;
   c. allowing the cells sorted into a 96-well plate to stand for 1 hr, and adding Pam3CK4, FSL-1, Flagellin, IL-7, IL-2, IL-15 as well as magnetic beads coated with an anti-human CD3 antibody and an anti-human CD28 antibody, wherein the ratio of the magnetic beads to the cells is 1:1; and the cells are placed in an incubator at 37° C. for one week; and
   d. transferring the cells in the 96-well plate to a 24-well plate in the second week, and then sequentially transferring the cells to a T25 cell culture flask, a T75 cell culture flask and a T175 cell culture flask according to the number of growing cells; and each time a culture dish is replaced, corresponding media and stimulants are supplemented until the desired number of cells is achieved.

7. The method according to claim 1, wherein sources of the PD-1+CD8+T cell subpopulations comprise peripheral venous blood from healthy subjects, HIV-1 infected individuals or tumor patients, lymphocytic leukemia, lung cancer, breast cancer, esophageal cancer, gastric cancer, liver cancer, uterine cancer, cervical cancer, renal cancer, pancreatic cancer, nasopharyngeal cancer, small intestine cancer, large intestine cancer, colorectal cancer, bladder cancer, bone cancer, prostate cancer, ovarian cancer, thyroid cancer, rhabdomyoma, leiomyoma and cerebroma, HIV infection, HBV infection, HCV infection, or *Mycobacterium tuberculosis* infection.

\* \* \* \* \*